United States Patent [19]

Noller

[11] Patent Number: 4,857,735
[45] Date of Patent: Aug. 15, 1989

[54] LIGHT EMITTING DIODE SPECTROPHOTOMETER

[76] Inventor: Hans G. Noller, 2631 Blueridge Ave., Orange, Calif. 92668

[21] Appl. No.: 113,230

[22] Filed: Oct. 23, 1987

[51] Int. Cl.[4] .......................................... G01J 3/42
[52] U.S. Cl. ............................... 250/339; 250/343; 356/217; 356/323
[58] Field of Search ............... 250/339, 343, 345, 341; 356/323, 319, 435, 217

[56] References Cited

U.S. PATENT DOCUMENTS

| | | | |
|---|---|---|---|
| 3,810,696 | 5/1974 | Hutchins, Jr. | 356/434 |
| 3,941,487 | 3/1976 | Ehret et al. | 356/414 |
| 4,092,069 | 5/1978 | Fukuda et al. | 356/434 |
| 4,118,625 | 10/1978 | Underwood | 250/343 |
| 4,133,873 | 1/1979 | Noller | 436/518 |
| 4,136,959 | 1/1979 | Honkawa et al. | 250/339 |
| 4,171,909 | 10/1979 | Kramer et al. | 356/435 |
| 4,236,826 | 12/1980 | Yamanishi | 356/432 |
| 4,240,751 | 12/1980 | Linnecke et al. | 250/526 |
| 4,243,883 | 1/1981 | Schwartzmann | 250/343 |
| 4,260,883 | 4/1981 | Onoda et al. | 250/345 |
| 4,357,105 | 11/1982 | Loretz | 356/414 |
| 4,420,566 | 12/1983 | Jessop et al. | 250/339 |
| 4,570,069 | 2/1986 | Gager | 250/343 |
| 4,637,730 | 1/1987 | Ponstingl et al. | 356/411 |

OTHER PUBLICATIONS

ELECTRONIC CIRCUITS-DISCRETE AND INTEGRATED, by Donald L. Schilling and Charles Belove, 1968 and 1979.
Solid-State Laser for the Experimenter, Forrest M. Mims, *Popular Electronics*, Oct. 1971.
Europium Phosphorescence as a Probe of Binding to Phospholipids, by Nils-Erik L. Saris Elsevier Scientific Publishers Ireland Ltd., 1983.
Fluoroimmunoassay: Present Status and Key Problems, by Erkki Soini and Ilkka Hemmila, Clinical Chemistry, vol. 25, No. 3, 1353-361, (1979).
Determination of Hemoglobin and its Derivatives, E. J. van Kampen and W. G. Zijlstra, Advances in Clinical Chemistry, vol. 8, 1965.
Notification of Final Adoption of an International Method and Standard Solution for Hemoglobinometry Specifications for Preparation of Standard Solution, Russell J. Eilers, M.D., *The American Journal of Clinical Pathology*, 1967.
Determination of Serum Albumin, by Basil J. Doumas. The Estimation and Clinical Significance of the Individual Plasma Proteins, pp. 335-338.
A Sensitive and Versatile Chromogenic Assay for Peroxidase and Peroxidase-Coupled Reactions, T. T. Ngo and Howard M. Lenhoff, Analytical Biochemistry 105, 389-397, (1980).
Application of a New Peroxide Indicator Reaction to the Specific, Automated Determination of Glucose with Glucose Oxidase, by Nathan Gochman and Joan M. Schmitz, *Clinical Chemistry*, vol. 28, No. 9, 1972.
Determination of Serum Calcium by Means of Ortho-cresolphthalein Complexone, by Harold V. Connerty, M.D., and Anglis R. Briggs, B.S., *The American Journal of Clinical Pathology*, vol. 45, No. 3, Jun. 21, 1965.
An Improved Automated Procedure for the Determination of Calcium in Biological Specimens, by Hillel J. Gitelman, *Analytical Biochemistry 18*, 521-531, (1967).

(List continued on next page.)

Primary Examiner—Janice A. Howell
Assistant Examiner—William F. Rauchholz
Attorney, Agent, or Firm—Knobbe, Martens, Olson & Bear

[57] ABSTRACT

A spectrophotometer incorporating a pulsed light emitting diode as a source of radiation. The light emitting diode emits substantially monochromatic light thus negating the need for a separate wavelength control. The spectrophotometer may incorporate a pair of light emitting diodes for performing bichromatic spectrophotometric determinations. The light emitting diodes are pulsed with a duty cycle and pulse amplitude such that it is possible to obtain a higher amplitude pulse than the light emitting diode could sustain at a continuous voltage input level. Continuous voltages at this level would damage the light emitting diode.

25 Claims, 3 Drawing Sheets

OTHER PUBLICATIONS

An Automated Procedure for the Simultaneous Determination of Calcium and Phosphorus, by Gerald Kessler and Morris Wolfman, *Clinical Chemistry*, vol. 10, pp. 686–703, 1964.

2-Amino-2-methyl-1-propanol as the Alkalizing Agent in an Improved Continuous-Flow Cresolphthalein Complexone Procedure for Calcium in Serum, by Wells R. Moorehead and Homer G. Biggs, *Clinical Chemistry*, 20/11, 1458–1460, (1974).

Vereinfachte Photometrische Methoden zur Bestimmung des Blutbilirubins, by L. Jendrassik und P. Grof, Eingegangen am, Mar. 1938.

Standardization in Bilirubin Assays: Evaluation of Selected Methods and Stability of Bilirubin Solutions, by Doumas, et al., Clinical Chemistry, vol. 19, No. 9, pp. 984–993, 1973.

A Study of Six Representative Methods of Plasma Bilirubin Analysis, by Derek Watson and Janice A. Rogers, Clin. Path., vol. 14, No. 3, May 1961.

Determination of Serum Calcium by Oxalate Precipitation and Redox Titration and The Determination of Serum Calcium by Precipitation with Chloranilic Acid, pp. 904–906.

Time-Resolved Fluoroimmunoassay of Human Choriogonadotropin, by Pettersson, et al., Clinical Chemistry, 29/1, 60–64, (1983).

LIGHT EMITTING DIODE SPECTROPHOTOMETER

BACKGROUND OF THE INVENTION

This invention pertains to spectrophotometers and to methods of spectrophotometric analysis, and more particularly to spectrophotometers incorporating light omitting diodes as a source of radiation and methods in which such spectrophotometers are used.

Spectrophotometers are used to determine the amount of a substance contained in a solution. For example, a spectrophotometer may be used to determine the amount of hemoglobin contained in a blood sample. It is known that the concentration of a particular substance in a solution is related to the amount of light that the solution absorbs. Thus, the concentration of the substance can be determined by measuring the amount of light absorbed by the solution. This relationship between the amount of a substance in solution and the quantity of light absorbed is strictly obeyed only when substantially monochromatic radiation is used.

A typical spectrophotometer consists of a source of radiation such as an incandescent lamp, a wavelength control separate from the source of radiation, a container for the sample solution, a light receptor, and circuitry which converts the amount of light received at the receptor to an appropriate indication of the absorbance. The wavelength control in such a spectrophotometer is usually either a color filter or a monochromator, such as a prism or grating. This wavelength control is incorporated into the spectrophotometer so that the relationship between the concentration and the light absorption is strictly obeyed.

A substance may absorb different amounts of light at different wavelengths. For example, a solution of titanium formed with hydrogen peroxide has a peak absorbance of 0.90 at a wavelength of approximately 410 nanometers. At shorter and longer wavelengths, the absorbance drops significantly. When using spectrophotometric analysis, it is desirable to test a substance at its peak absorption wavelength because this will yield the most accurate results. Since different substances have peaks of absorption at different wavelengths, spectrophotometers have a number of color filters or other mechanisms for producing monochromatic light at various wavelengths.

One problem with spectrophotometers is that the wavelength control is complicated, expensive, and subject to errors. Where color filters are used for the wavelength control, a spectrophotometer must have many color filters as well as mechanisms to position these color filters. Where monochromators such as prisms or gratings are used, the positioning means for the prism or grating must be very accurate, since misalignment results in radiating the sample with a shorter or longer wavelength of light than intended, thus causing errors in determining the amount of sample present.

SUMMARY OF THE INVENTION

The present invention is directed to a novel spectrophotometer in which the need for a separate wavelength control has been obviated. The source of radiation used in the spectrophotometer is a light emitting diode, which emits substantially monochromatic radiation.

Another feature of the present invention is a method of spectrophotometric analysis in which the testing solutions have absorbance maxima at substantially identical wavelengths of light. This method of spectrophotometric analysis obviates the need for expensive wavelength control systems.

This method of spectrophotometric analysis includes passing light from a light emitting diode through a solution; detecting the light after it passes through the solution; generating a signal representative of the intensity of the light detected in the detecting step; generating from the signal an indication of the intensity of the light; and performing each of the above-described steps for each solution in a group of solutions, the solutions having spectrophotometric absorbance maxima within the band of wavelengths of light emitted by the light emitting diode. This group of solutions may comprise a first solution containing ferricyanide and KCN; a second solution containing dimethylaminobenzoic acid, 3-dimethylaminobenzoic acid, glucose oxidase, and peroxidase; a third solution containing diazotized sulfanilic acid; a fourth solution including bromcresol green solution; a fifth solution including phenolphthalein monophosphate solution with $MgCl_2$; and a sixth solution including orthocresolphthalein complexone and buffered diethylamine.

A further feature of the present invention provides an apparatus and a method for simultaneously testing more than one solution for the presence of multiple substances. The novel method includes the steps of passing light from a first light emitting diode through a first solution; detecting a light emitted from the first light emitting diode; generating a first signal representative of the intensity of the light detected by the first light emitting diode; passing light from a second light emitting diode through a second solution; detecting the light emitted from the second light emitting diode; generating a second signal representative of the intensity of the light detected by the second light emitting diode; generating a signal representative of the difference in intensities of the light detected by the first and second light emitting diodes; and generating an indication representative of the difference in the intensities of light detected by the respective light emitting diodes. This method is particularly advantageous for the simultaneous testing of hemoglobin type A and hemoglobin type B.

DESCRIPTION OF THE PREFERRED EMBODIMENT

Figure 1:
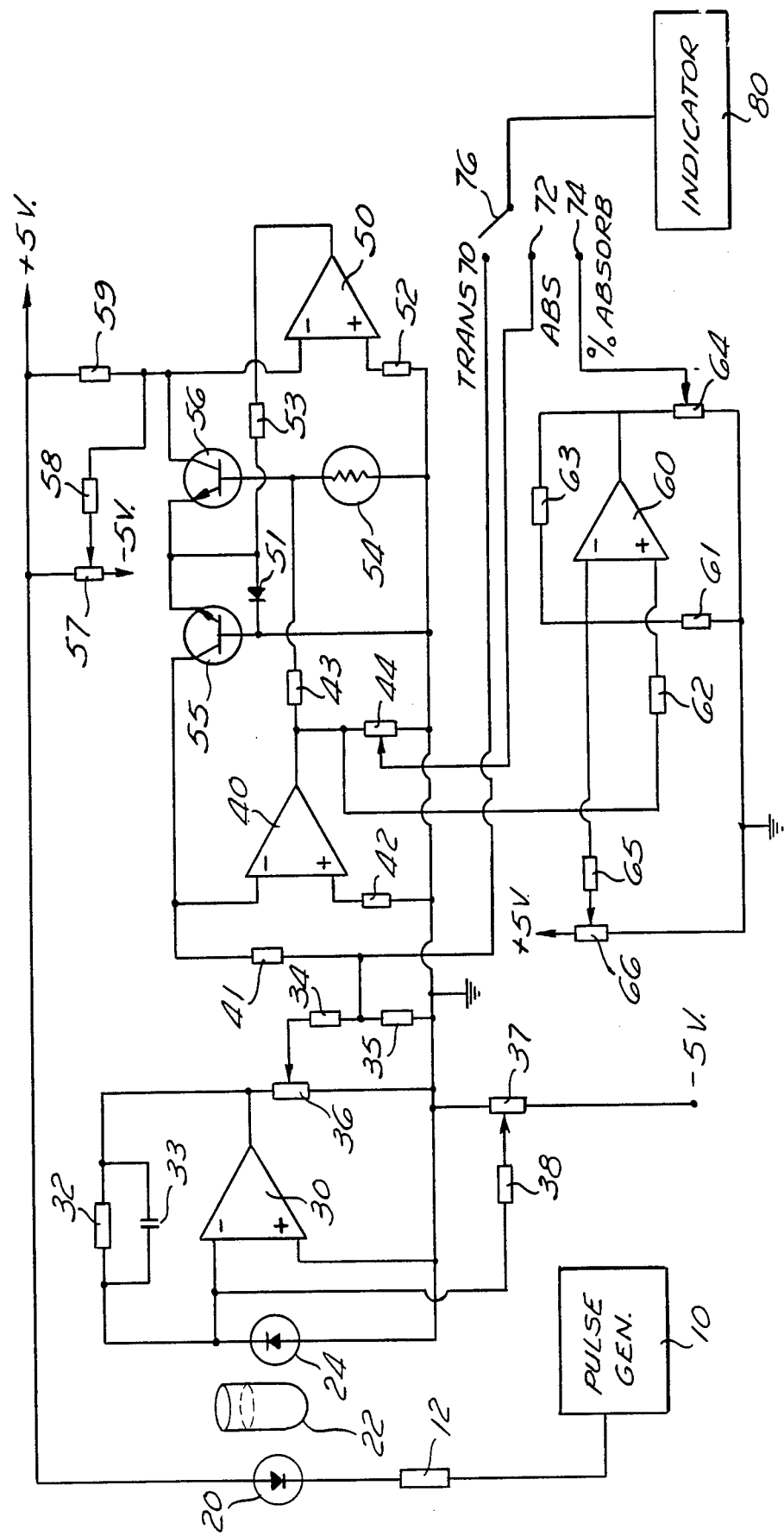
FIG. 1 illustrates a spectrophotometer in accordance with one embodiment of the present invention.

One embodiment of the present invention is illustrated in FIG. 1. This first embodiment consists of five basic circuit parts. The first part of the circuit consists of a pulse generator 10 coupled to a light emitting diode 20 through a resistor 12. The light emitting diode 20 is in close enough proximity to a cuvette 22, which contains the solution to be tested, so that the sample may be sufficiently radiated. The light emitting diode 20 is repeatedly switched off and on during the analysis procedure. The switching is accomplished by feeding a train of pulses to the diode 20 from the pulse generator 10.

The pulse train preferably has a small duty cycle so that relatively large voltages can be transmitted to the diode 20 for brief periods of time. Using a small duty cycle pulse train with relatively high amplitude pulses insures that the diode 20 will radiate with sufficient intensity yet will not burn out. It has been determined that a pulse train with a duty cycle of approximately 0.1 to 1 percent and having an amplitude of approximately 4 volts is preferable to use in operating the spectrophotometer. With this duty cycle and pulse amplitude, it is possible to obtain higher amplitude pulses than the light emitting diode could sustain at a continuous voltage input level. Continuous voltages at this level would damage the light emitting diode. This pulse train is provided at an approximate frequency of 20K cycles per second. This pulse train can be satisfactorily produced by a TI 555 pulse generator manufactured by Texas Instruments.

Any number of commercially available light emitting diodes may be used. The TIL209A, which is manufactured by Texas Instruments, emits red visible light with a wavelength at peak emission between approximately 630 and 670 nanometers. The TIL211 emits green light with a typical wavelngth at peak emission of approximately 570 nanometers. An amber diode such as the TIL281 emits light with a wavelength between approximately 580 and 600 nanometers. Blue diodes which emit light with a wavelength of approximately 490 nanometers may also be used, as well as diodes in the infrared portion of the spectrum, such as the TIL31, which emits infrared radiation at a wavelength of about 940 nanometers.

The photodetector used depends upon the type of light emitting diode which is used. When a light emitting diode is used which emits in the visible portion of the spectrum, a commercially available photodetector such as a 157201 which is commercially available from Vactec of St. Louis, Mo., should be used. When a diode which emits in the infrared portion of the spectrum is used, a B2M photodetector commercially available from International Rectifier should be used.

The second part of the circuit detects the light which passes through the testing solution in the cuvette 22 and generates a signal representation of the transmittance. The radiation transmitted by the light emitting diode 20 through the cuvette 22 is detected by a photodetector 24, which generates a signal representative of the amount of radiation received. This signal is fed to the inverting input of an operational amplifier 30 and is output through potentiometer 36 connected to ground. A resistor 32 and a capacitor 33 are coupled in parallel between the inverting input and the output of the operational amplifier 30. A resistor 38 is coupled between the inverting input of the amplifier 30 and a potentiometer 37, which is coupled between ground and −5 volts. The noninverting input of the amplifier 30 is connected to ground. The amplified signal passes through the voltage divided output of the potentiometer 36 through a resistor 34 and another resistor 35 connected to ground. An output line 70 is coupled to the junction of the resistors 34 and 35 to read the voltage at this point.

The junction between the resistors 34 and 35 is also coupled through a resistor 41 to the inverting input of an operational amplifier 40. The noninverting input of the operational amplifier 40 is coupled to a resistor 42 which is coupled to ground. The output of the amplifier 40 is connected to a potentiometer 44 connected to ground. The output of the operational amplifier 40 is also connected to a resistor 43 which is connected to the base of a transistor 56 and a temperature-compensated resistor 54 connected to ground. The collector of the transistor 56 is coupled to the inverting input of an operational amplifier 50 as well as to a resistor 58 and a resistor 59. The resistor 59 is connected to a +5 volt power supply and the resistor 58 is connected to a potentiometer which is connected between a +5 volt supply and a −5 volt supply. The emitter of the transistor 56 is coupled to the emitter of another transistor 55. These emitters are coupled to a diode 51 connected to ground and to the output of the operational amplifier 50 through a resistor 53. The noninverting input of the amplifier 50 is connected to ground through a resistor 52. The collector of the transistor 55 is coupled to the inverting input of the operational amplifier 40 and the base of the transistor 55 is coupled to ground. This part of the circuit, which comprises the operational amplifiers 40 and 50 and the transistors 55 and 56 along with the accompanying resistors, acts as a temperature-compensated logarithmic amplifier. An output line 72 is connected to a potentiometer 44 to receive the output of this part of the circuit.

A fourth part of the circuit acts to convert the signal which represents absorbance into a signal representative of the percent absorbance. This circuit comprises of an operational amplifier 60 with its noninverting input coupled through a resistor 62 to the output of the operational amplifier 40. The inverting input to the amplifier 60 is connected to a resistor 61 connected to ground and a resistor 65. The resistor 65 is coupled to a potentiometer 66 connected between a +5 volt power supply and ground. A resistor 63 is connected between the inverting input and the output of the operational amplifier 60. An output line 74, which represents percent absorbance, is coupled to a potentiometer 64 connected between the output of the operational amplifier and ground.

The last part of the spectrophotometer circuit consists of a switch 76 and a conventional indicator 80 for converting the transmittance, absorbance, and percent absorbance signals into a visual display. The indicator 80 may comprise a well known LED numeric display such as the Texas Instruments TIL312.

The transmittance, absorbance, and percent absorbance are related. The transmittance is defined as the amount of light transmitted through the sample in relation to the amount of light incident upon the sample. The absorbance is defined as the logarithm of the inverse of the transmittance, i.e. absorbance=log (1/transmittance). Thus, the concentration of a substance in a solution may be determined from the transmittance, absorbance, or the percent absorbance.

In order to use the spectrophotometer described in this embodiment, the switch 76 is set to one of the output lines 70, 72, or 74, depending on whether the transmittance, the absorbance, or the percent absorbance, respectively, is desired. The spectrophotometer is then calibrated with a blank solution by adjusting the potentiometer 36. A known volume of the sample to be tested is then introduced into the blank solution in the cuvette 22 and the absorbance is determined after mixing. In this manner the quantity of the substance introduced can be calculated.

Different substances have peaks of absorption at different wavelengths of light. When the quantity of a substance is to be determined by spectrophotometric analysis, the substance should be radiated with radiation of a wavelength at which the substance has an absorptive peak, since this results in the most accurate determination. A preferred embodiment of the present invention incorporates a diode which emits substantially monochromatic light. The present invention is practiced by using a particular set of chemistries to produce absorptive peaks at a single wavelength of light, the wavelength generated by the light emitting diode. The following set of reagents has been developed for a spectrophotometer incorporating a light emitting diode which emits light substantially of approximately 570 nanometers. When each of these reagents is combined with the particular substance to be tested, an absorbance peak will be present at approximately 570 nanometers.

Doctors frequently desire to determine the amount of hemoglobin contained in a blood sample. Hemoglobin in the blood can be oxidized to methemoglobin by ferricyanide and converted by KCN into stable cyanmethemoglobin. The reagent which, when combined with hemoglobin, causes an absorbance peak at 570 nanometers is known as Drabkin solution and consists of 200 milligrams of $K_3Fe(CN)_6$, 50 milligrams of KCN, and 1000 milligrams of $NaHCO_3$ per 1000 milliliters of distilled water. Three thousand microliters of this reagent solution are used as a blank solution for calibration, and then 20 microliters of the blood sample are introduced into this blank solution to perform the spectrophotometric analysis.

When albumin is being photometrically tested for bromcresol green binding is used. Bromcresol green binds very tightly to the albumin molecular, almost independent of the ionic strength and of the pH. The color of the bound form of the albumin is different from that of the albumin substance itself, thus allowing the photometric determination to occur at 570 nm. To determine the amount of albumin in a solution, a blank solution consisting of 0.15 millimolar bromcresol green solution in 0.1 molar succinate buffer with a pH of 4.15 is used. Three thousand microliters of this blank solution are used for calibration purposes and 10 microliters of the sample unknown are later added for analysis purposes.

Glucose is oxidized through double enzymatic action when reacted with glucose oxidase and peroxidase. The hydrogen peroxide produced in the first step of this reaction is converted in the second step by the peroxidase into a product whose color is proportional to the concentration of the glucose. To test for glucose at 570 nanometers, a blank solution consisting of 1000 microliters of 4 millimolar dimethylaminobenzoic acid, 1000 microliters of 600 micromolar 3-dimethylaminobenzoic acid and 1000 microliters of glucose oxidase (100 units/ml) and peroxidase (30 units/ml) is used. Ten microliters of the unknown sample are added to this blank solution for testing purposes.

When calcium is to be tested for, a calcium containing serum sample is reacted with diethylamine buffered orthocresolphthalein complexone, and the serum thereby develops a color proportional to the amount of calcium in the solution. Calcium is tested for by using 3000 microliters of 0.1 molar diethylamine buffer and 300 microliters of orthocresolphthalein complexone as a blank solution. Five microliters of the unknown sample are then added to this blank solution for testing purposes.

When bilirubin is tested for, diazotized sulfanilic acid is added to the bilirubin-containing sample to form a strongly alkaline tartrate solution which converts the purple azobilirubin into the blue azobilirubin which may then be tested at 570 nm. The addition of caffeine and sodium benzoate accelerates the above reaction. Bilirubin is tested with a blank solution consisting of 3000 microliters of 0.70 molar sodium acetate, 0.20 molar caffeine, and 0.40 molar sodium benzoate, along with 300 microliters of 0.02 molar sodium nitrite activated sulfanilic acid in 0.1 molar hydrochloric acid. One hundred microliters of the bilirubin-containing sample are added to the blank solution for testing purposes.

When alkaline phosphatase is tested for, the serum sample is interacted with well buffered, approximately 9.5 pH phenolphthalein-monophosphate-monopyridine salt solution, which acts as a substrate for the alkaline phosphatase which is itself colorless. Under the influence of the alkaline phosphatase, the serum develops a pink color with an intensity which is related to the concentration of the alkaline phosphatase in the serum. The absorbance can be determined at a wavelength of 570 nm. Alkaline phosphatase can be tested by using a blank solution consisting of 3000 microliters of 0.05% phenolphthalein monophosphate solution containing 0.1 molar $MgCl_2$. Fifty microliters of the sample are introduced to the blank solution for testing purposes. The sample-containing blank solution should be read at 570 nm after an incubation time at room temperature of exactly 30 minutes, or after 10 minutes at 37° centigrade. The color development can be stopped after the precise incubation period by adding 500 $\mu l$ of 5% sodium pyrophosphate.

Figure 2:
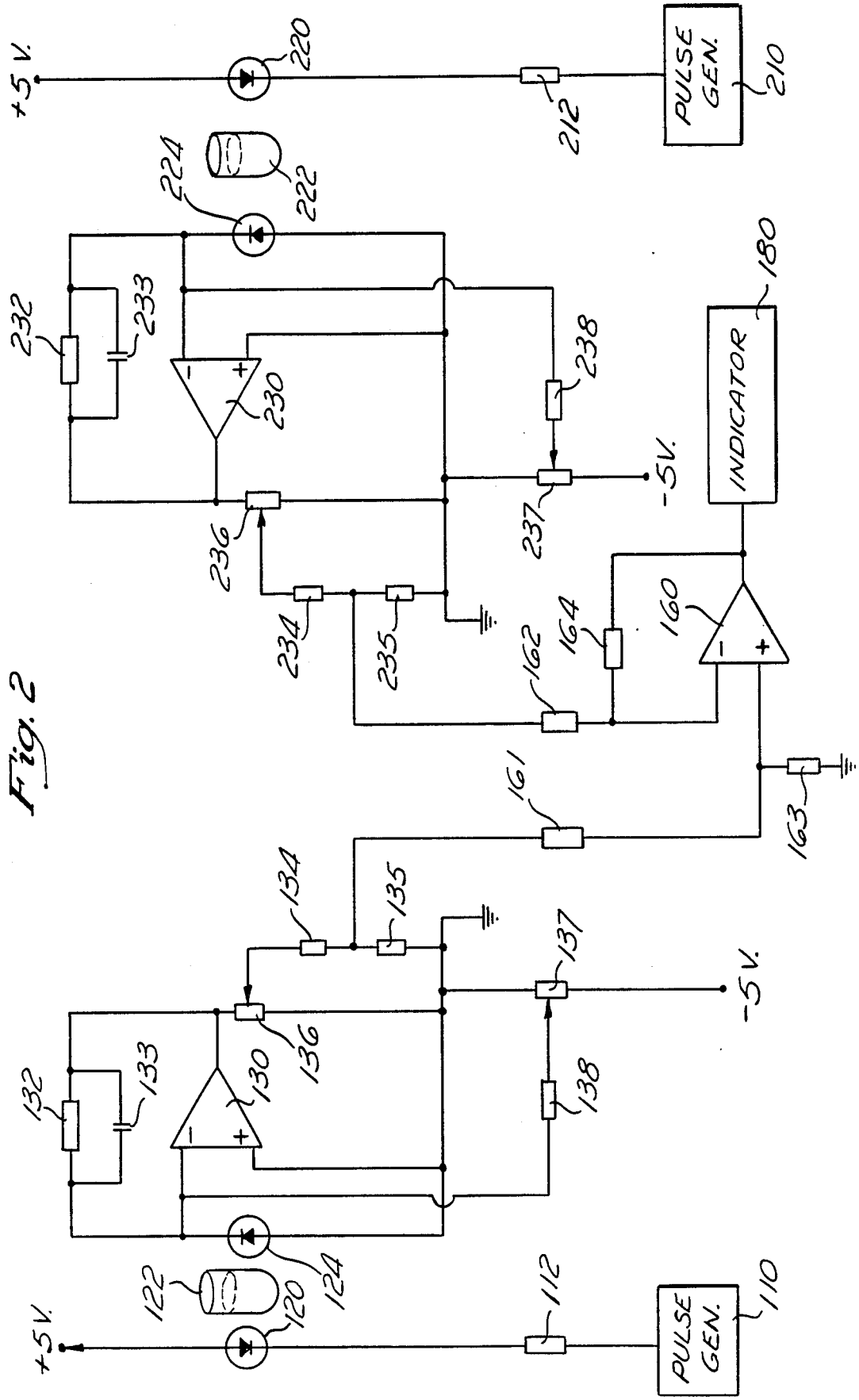
FIG. 2 illustrates a spectrophotometer in accordance with a second embodiment of the present invention.

A second embodiment of the present invention is illustrated in FIG. 2. This embodiment is used to perform bichromatic analyses. In the spectrophotometer illustrated in FIG. 2, two testing solutions are simultaneously radiated by a pair of light emitting diodes 120 and 220. Operational amplifiers 130 and 230 generate a pair of signal derived from photodetectors 124 and 224 respectively. The signals generated by the operational amplifiers 130 and 230 are fed to a difference amplifier 160 which generates a signal representative of the difference in the absorbance of radiation of the two testing solutions contained in the cuvettes 122 and 222. This "difference" signal is then fed to an indicator 180 which provides a visual display of the difference in intensities.

More specifically, a pulse generator 110 provides a stream of pulses through resistor 112 to periodically excite a light emitting diode 120. A photodetector 124 detects the light emitted by the light emitting light diode 120 through the solution to be tested in the cuvette 122. The photodetector 124 generates a signal fed to the inverting input of an operational amplifier 130. A resistor 132 and a capacitor 133 are coupled in parallel between inverting input and the output of the operational amplifier 130. The inverting input is also coupled to a potentiometer 137 through a resistor 138. The output of the operational amplifier 130 is fed through a potentiometer 136, a resistor 134, and a resistor 135.

The operation of the circuit shown in the right-hand portion of FIG. 2 is the same. A pulse generator 210 emits a stream of pulses through a resistor 212 to periodically excite a light emitting diode 220. A photodetector 24 detects the light received from the diode 220 and feeds a signal to the inverting input of an operational amplifier 230, which outputs a signal through a potentiometer 236, a resistor 234, and a resistor 235. A resistor 232 and a capacitor 233 are coupled in parallel between the inverting input and the output of the operational amplifier 230, and the inverting input of the operational amplifier 230 is also coupled to a potentiometer 237 through a resistor 238.

The last portion of this second embodiment consists of a difference amplifier 160 and an indicator 180. The difference amplifier 160 receives two signals, one from between resistors 134 and 135 and another from between the resistors 234 and 235. These signals are representative of the amount of light which passes through the solutions contained in the cuvettes 122 and 222, respectively. The difference amplifier 160, biased by four resistors 161, 162, 163, and 164, generates a signal representative of the difference in intensities of light absorbed by the two solutions. An indicator 180 accepts this difference signal and generates a visual display of the difference.

Figure 3:
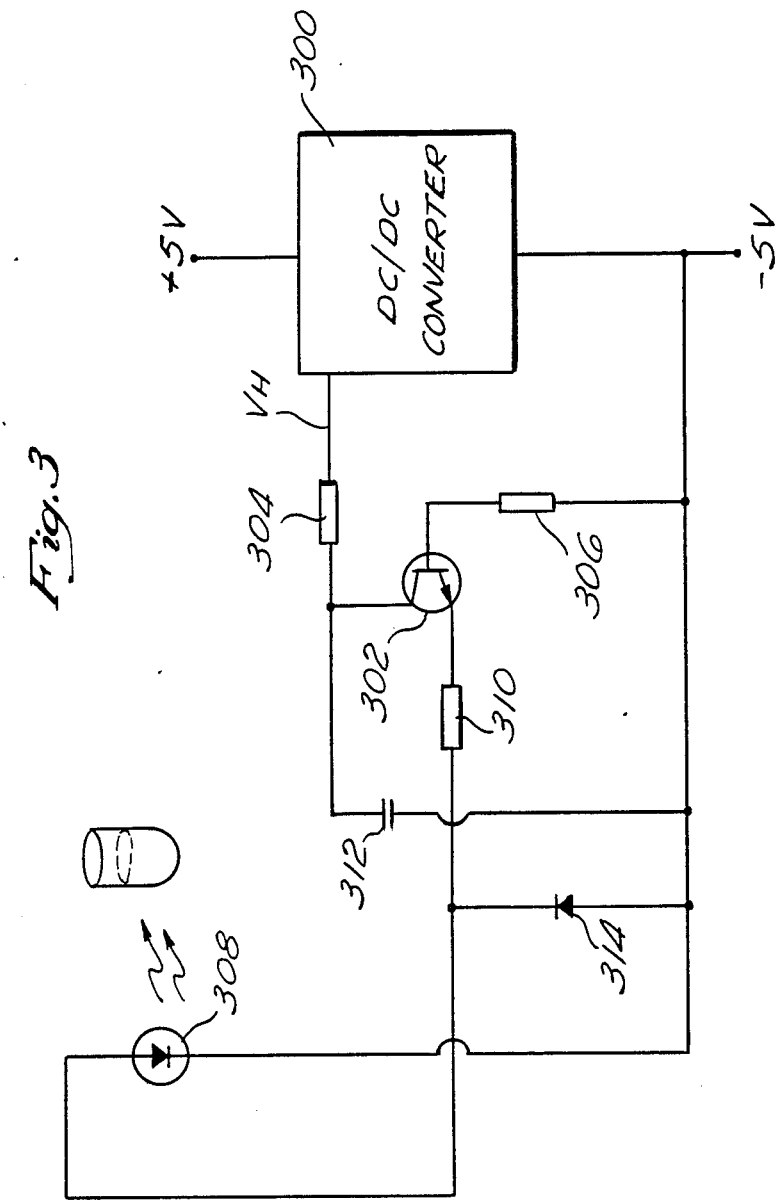
FIG. 3 illustrates a spectrophotometer, including a laser diode, in accordance with another embodiment of the present invention.

In another embodiment of the invention, an avalanching transistor circuit is used in place of the combination of the resistor 12 and pulse generator 10. Now referring to FIG. 3, this alternative circuit comprises a DC-DC converter 300 connected to the collector of an avalanching transistor 302 through a resistor 304. A resistor 306 is coupled to the base of the transistor 302, and the emitter of the transistor 302 is coupled to a laser diode 308 through a resistor 310. The circuit also includes a capacitor 312 connected across the transistor 302 and a diode 314 connected to the emitter of the transistor 302. In operation, the DC-DC converter 300 generates a high voltage, indicated in FIG. 3 as $V_H$, which causes the voltage on the capacitor 312 to increase until the breakdown voltage of the transistor 302 is reached, at which point the capacitor 312 discharges through the collector-emitter path of the transistor 302, causing a relatively large current spike to be delivered to the laser diode 308 for a short period of time. The laser diode 308 may be a TA7606 diode commercially available from RCA. This embodiment is advantageous in that a high signal-to-noise ratio is provided, and is also particularly advantageous in fluorescent applications.

Modifications and alternative embodiments of the invention will be apparent to those skilled in the art in view of the foregoing description. This description is to be construed as illustrative only, and is for purposes of teaching those skilled in the art the best mode of the invention. The details of the structure may be varied substantially without departing from the spirit of the invention, and the exclusive use of all modifications which come within the scope of the appended claims is reserved.

What is claimed is:

1. A spectrophotometer with a high signal to noise ratio, comprising:
    a first light emitting diode for emitting light through a solution having a spectrophotometric absorbance maximum within the band of wavelengths of light emitted by said light emitting diode;
    a first pulse generator connected to said light emitting diode, said pulse generator providing pulses having a duty cycle and voltage selected so that said light emitting diode emits light of higher intensity during pulses generated by said pulse generator than that maximum intensity that said light emitting diode could produce with a continuous voltage without damage to said light emitting diode;
    a photodetector optically coupled to said light emitting diode for detecting light emitted from said light emitting diode and passed through said solution; and
    a first signal generator coupled to said photodetector for generating a signal representative of the intensity of the light detected by said photodetector.

2. A spectrophotometer as claimed in claim 1 wherein said light emitting diode emits radiation with a wavelength in the infrared region of the light spectrum.

3. A spectrophotometer as claimed in claim 1 wherein said light emitting diode emits light in the visible portion of the light spectrum.

4. A spectrophotometer as claimed in claim 1 wherein said light emitting diode emits light with a wavelength of approximately 570 nanometers.

5. A spectrophotometer as claimed in claim 1, additionally comprising a first signal converter coupled to said signal generator for providing a second signal representative of the absorbance of the solution of the light emitted by said light emitting diode.

6. A spectrophotometer as claimed in claim 5 additionally comprising a second signal converter coupled to said first signal converter, for providing a third signal representative of the percent absorbance of the solution of the light emitted by said light emitting diode.

7. A spectrophotometer as claimed in claim 6 wherein said second signal converter is coupled to said first signal converter.

8. A spectrophotometer as claimed in claim 7 wherein said first signal converter comprises an operational amplifier.

9. A spectrophotometer as claimed in claim 8 wherein said first signal converter comprises a logarithmic amplifier.

10. A spectrophotometer as claimed in claim 9 wherein said logarithmic amplifier is temperature compensated.

11. A spectrophotometer as claimed in claim 10 wherein said second signal converter comprises an operational amplifier.

12. A spectrophotometer as claimed in claim 1 wherein said pulse generator provides a pulse stream having a duty cycle of approximately 0.1 to 1 percent, and an amplitude of approximately 4 volts.

13. A spectrophotometer as claimed in claim 12 wherein said spectrophotometer includes an indicator coupled to said first signal generator for providing an indication representative of the intensity of the detected light, said indicator includes an array of light emitting diodes, said array constructed to display a numeral representing the amount of light detected by said photodetector.

14. A spectrophotometer as claimed in claim 1 additionally comprising:
    a second light emitting diode for emitting light through a second solution having a spectrophotometric absorbance maximum within the band of wavelengths of light emitted by said second light emitting diode;
    a second pulse generator connected to said second light emitting diode, said pulse generator providing pulses having a duty cycle and voltage selected so that said light emitting diode emits light of higher intensity during pulses generated by said pulse generator than that maximum intensity that said light emitting diode could produce with a continuous voltage without damage to said light emitting diode;
    a second photodetector optically coupled to said second light emitting diode for detecting light emitted from said second light emitting diode and passed through said second solution;

a second signal generator coupled to said second photodetector for generating a signal representative of the intensity of the light detected by said second photodetector;

a third signal generator for generating a third signal representative of the difference in the intensities of the light detected by said photodetectors; and an indicator coupled to said first and second generators through said third generator in order to provide an indication representative of the intensity of the detected light.

15. A spectrophotometer as claimed in claim 14 wherein said second signal generator comprises an operational amplifier and said third signal generator comprises a difference amplifier.

16. A high signal to noise spectrophotometer comprising:
   a laser diode for emitting radiation through a solution having a spectrophotometric absorbance maximum within the band of wavelengths emitted by said laser diode;
   a pluse generator connected to said laser diode said pulse generator providing pulses having a duty cycle and voltage selected, so that said laser diode emits higher intensity radiation during pulses generated by said pulse generator then that maximum intensity that said laser diode could produce with a continuous voltage without damage to said laser diode;
   a photodetector, positioned so it that detects the main portion of the direct beam of radiation emitted by said laser diode, the main portion being partially absorbed when passed through said solution; and
   a first signal generator coupled to said photodetector for generating a signal representative of the intensity of the radiation detected by said detector.

17. A method of optically measuring properties of a solution comprising the steps of:
   (a) pulsing a light emitting diode with pulses having a duty cycle and voltage selected so that said light emitting diode emits light of higher intensity during pulses generated by said pulse generator than that maximum intensity that the light emitting diode could produce with a continuous voltage;
   (b) passing light from the light emitting diode through a first solution;
   (c) detecting the light after it passes through said first solution;
   (d) generating a first signal representative of the intensity of the light detected in said detecting step; and
   (e) generating from said first signal an indication relating to the intensity of the light detected.

18. A method as claimed in claim 17, comprising an additional step:

(f) performing each of said steps (a) through (d) for each solution in a group of solutions, said solutions in said group having spectrophotometric absorbance maxima within the band of wavelengths of light emitted by said light emitting diode, said group of solutions comprising:
   a first solution containing ferricyanide and KCN;
   a second solution containing dimethylaminobenzoic acid, 3-dimethylaminobenzoic acid, glucose oxidase, and peroxidase; and
   a third solution containing diazotized sulfanilic acid.

19. A method as claimed in claim 18, wherein said group additionally comprises:
   a fourth solution including bromcresol green solution;
   a fifth solution containing phenolphthalein monophosphate solution with $MgCl_2$; and
   a sixth solution containing orthocresolphthalein complexone and buffered diethylamine.

20. A method as claimed in claim 18 wherein said light emitting diode emits light with a wavelength of approximately 570 nanometers.

21. A method as claimed in claim 17 wherein said light emitting diode in said step (a) emits radiation with a wavelength in the infrared region of the light spectrum.

22. A method as claimed in claim 17 wherein said light emitting diode emits light with a wavelength of approximately 490 nanometers.

23. A method as claimed in claim 17 wherein said light emitting diode emits light with a wavelength between approximately 580 and 600 nanometers.

24. A method as claimed in claim 17 wherein said light emitting diode emits light with a wavelength between approximately 630 and 670 nanometers.

25. A method as claimed in claim 17 additionally comprising the steps of:
   (f) pulsing a second light emitting diode with pulses having a duty cycle and voltage selected so that said second light emitting diode emits light of higher intensity during pulses generated by said pulse generator than that maximum intensity that the light emitting diode could produce with a continuous voltage without damage to the second light emitting diode;
   (g) passing light from the second light emitting diode through a second solution;
   (h) detecting the light emitted from said second light emitting diode after it passes through said second solution;
   (i) generating a second signal representative of the intensity of the light detected in said step (h); and
   (j) generating a third signal which is representative of the difference in the intensities of the light detected in said steps (c) and (h),
   said indication being generated directly from said third signal and indirectly from said first and second signals.

* * * * *